United States Patent [19]

Cross et al.

[11] 4,130,645
[45] Dec. 19, 1978

[54] FUNGICIDAL PHENYLNITRAMINES AND NEW PHENYLNITRAMINES

[75] Inventors: Barrington Cross, Rocky Hill; David H. Dawe, Hightstown, both of N.J.

[73] Assignee: American Cyanamid Company, Stamford, Conn.

[21] Appl. No.: 879,340

[22] Filed: Feb. 21, 1978

[51] Int. Cl.$^2$ ............... A61K 31/535; A61K 31/135; C07C 79/00; C07D 295/22

[52] U.S. Cl. .................................... 424/226; 71/121; 424/226; 424/304; 424/324; 424/330; 260/143; 260/397.6; 260/465 D; 260/465 E; 260/465 R; 260/558 R; 260/576; 260/578; 260/583 C; 560/24; 560/25; 560/30; 560/38

[58] Field of Search ............ 260/141 AN, 583 C, 576, 260/578, 397.6, 465 R, 465 E, 465 D, 558 R, ; 560/24, 25, 30, 38; 424/226, 304, 324, 330, 248; 71/121

[56] References Cited

U.S. PATENT DOCUMENTS 3,844,762  10/1974  Cross et al. .......................... 71/121

OTHER PUBLICATIONS

Chemical Abstracts, vol. 62, col. 16904 d, (1965), (abst. of Fr. Pat. No. 1,388,762.
Chemical Abstracts, vol. 55, cols. 7842 to 7843, (1961), (abst. of Frankel et al., U.S. Pat. No. 2,967,198).
Jones et al., Chemical Abstracts, vol. 48, cols. 5300 to 5301, (1954).
Romberg, Rec. Trav. Chim., vol. 8, pp. 273, 276–282, (1889).
White et al., J. Org. Chem., vol. 26, pp. 4124 to 4126, (1961).
Bamberger, Ber. Deut. Chem., vol. 53, pp. 2321 to 2327.
Dadieu et al., Monatshefte fur Chemie, vol. 57, pp. 225, 232–233 & 238,(1931).
Beilstein's Handbuch der Organischen Chemie, 4th Ed., vol. 16, pp. 697–698, Verlag Von Julius Springer, (Berlin, 1933), (Main Werke).
Beilstein's Handbuch der Organischen Chemie, 4th Ed., vol. 12, pp. 660–675 & 683–684, Verlag Von Julius Springer, (Berlin 1929), (Main Werke).

*Primary Examiner*—John D. Randolph
*Attorney, Agent, or Firm*—H. G. Jackson

[57] ABSTRACT

The present invention relates to novel methods for the protection of agricultural crops against plant pathogenic fungi comprising applying to the foliage of said crops a fungicidally effective amount of a compound selected from certain substituted phenylnitramines and certain novel salts of 2,3,5,6-tetrachlorophenylnitramine.

The present invention further relates to certain novel substituted phenylnitramine and certain novel salts of 2,3,5,6-tetrachlorophenylnitramine and methods of preparation thereof.

24 Claims, No Drawings

FUNGICIDAL PHENYLNITRAMINES AND NEW PHENYLNITRAMINES

The herbicidal properties of phenylnitramines and their use for the control of weeds is described in U.S. Pat. No. 3,844,762, issued Oct. 29, 1974 (to B. Cross et. al.) in which novel methods for the control of undesired plant species are disclosed by employing certain substituted phenylnitramines. The geotropic response of roots of rape and ryegrass, and the selective reduction of root growth when seeds of said plants are grown in the presence of phenylnitramines is described by R. L. Jones et. al., *J. Sci. Food Agric.* 5, 38 (1954). The effect of 2,4,6-tribromophenylnitramine and 2-chloro-9-fluorenol-9-carboxylic acid applied pre-emergence to groundsel and chickweed is described by W. Templeman, *Proc. Brit. Weed Control Conf.* 1, 3 (1954). He states, that although weed control is achieved at 11.2 and 16.8 kg/ha, these compounds possess very little selectivity and most crops which have been examined, have also proved to be susceptible. None of the above references anticipate, however, the novel foliar fungicidal activity of substituted phenylnitramines (hereinafter also referred to as N-nitroanilines) and certain novel salts of 2,3,5,6-tetrachlorophenylnitramine, nor indeed is such activity predictable therefrom.

This invention relates to the use of substituted phenylnitramines and certain novel salts of 2,3,5,6-tetrachlorophenylnitramine for the protection of agricultural crops against pathogenic fungi. More particularly, it relates to the control of plant pathogenic fungi by applying to the foliage of agricultural crops a fungicidally effective amount of a compound selected from the aforesaid phenylnitramines and novel salts of 2,3,5,6-tetrachlorophenylnitramine.

This invention further relates to novel, substituted phenylnitramines and novel salts of 2,3,5,6-tetrachlorophenylnitramine and methods of preparation thereof.

The substituted phenylnitramines and novel salts of 2,3,5,6-tetrachlorophenylnitramine of the present invention are defined and described as follows:

The fungicidal phenylnitramines of the present invention may be represented by formula

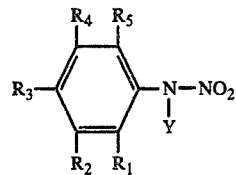

(I)

wherein the R groups $R_1$ and $R_5$ each represent a member selected from the group consisting of hydrogen, halogen, $C_1$–$C_4$ alkyl, halo($C_1$–$C_4$)alkyl, $C_1$–$C_4$ alkylthio, $C_1$–$C_4$ alkylsulfonyl, $C_1$–$C_4$ alkanoylamino,

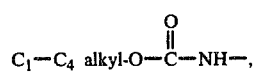

cyano and nitro; Y is a member selected from the group consisting of hydrogen, $C_1$–$C_8$ alkyl, $C_3$–$C_5$ alkenyl, $C_3$–$C_5$ alkynyl,

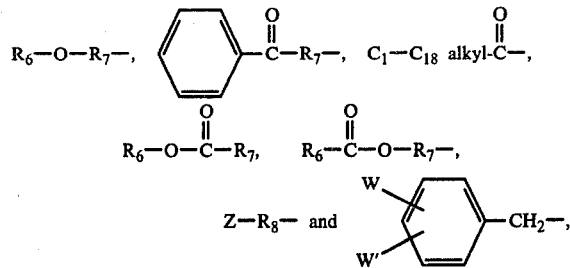

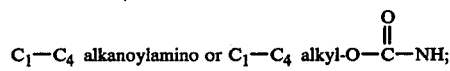

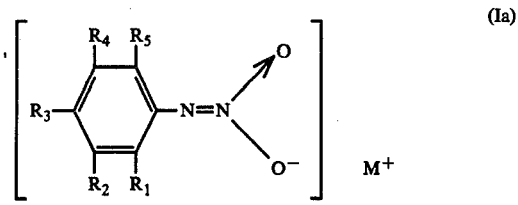

wherein $R_6$ is $C_1$–$C_4$ alkyl, $C_3$–$C_5$ alkenyl or $C_3$–$C_5$ alkynyl; $R_7$ is $C_1$–$C_4$ alkylene; $R_8$ is $C_2$–$C_4$ alkylene; W and W' each are hydrogen or halogen; Z is hydroxy or halogen; with the provisos, that at least two of the R groups $R_1$ to $R_5$ are other than hydrogen; and that not more than two of the R groups $R_1$ to $R_5$ can be $C_1$–$C_4$ alkylthio, $C_1$–$C_4$ alkylsulfonyl, nitro, cyano, $$C_1\text{–}C_4 \text{ alkanoylamino or } C_1\text{–}C_4 \text{ alkyl-O}\overset{\overset{\text{O}}{\|}}{\text{C}}\text{—NH};$$

and when Y is hydrogen, salts thereof may be formed, which may be graphically illustrated by formula (Ia) as follows:

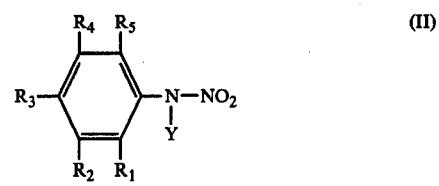

(Ia)

wherein $R_1$ to $R_5$ are as hereinabove defined; M represents an alkali metal, an alkaline earth metal and $NH_4$.

Certain members of the fungicidal phenylnitramines illustrated and defined by formula (I) above, are novel, and may be graphically illustrated by formula (II) and described in detail as follows:

(II)

wherein the R groups $R_1$, $R_2$, $R_4$ and $R_5$ each are selected from hydrogen, bromine and chlorine; $R_3$ is selected from hydrogen, $$C_2\text{–}C_3 \text{ alkanoylamino and } C_1\text{–}C_4 \text{ alkyl-O}\overset{\overset{\text{O}}{\|}}{\text{C}}\text{—NH—};$$

Y is selected from hydrogen, $C_3$–$C_5$ alkenyl, $C_3$–$C_5$ alkynyl,

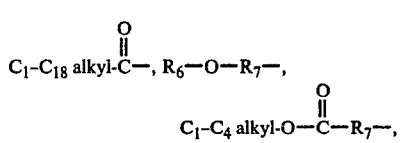

-continued

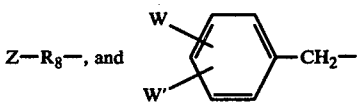

wherein $R_6$ is $C_3$-$C_5$ alkenyl or $C_3$-$C_5$ alkynyl; $R_7$ is $C_1$-$C_4$ alkylene; $R_8$ is $C_2$-$C_4$ alkylene; W and W' each are hydrogen or halogen; Z i hydroxy or halogen; with the provisos:

(1) that when Y is hydrogen, $R_3$ must not be hydrogen; and
(2) that at least two of the R groups $R_1$ to $R_5$ are other than hydrogen.

The noval fungicidal salts of 2,3,5,6-tetrachlorophenylnitramine of the present invention may be graphically illustrated and described by formula (III) as follows:

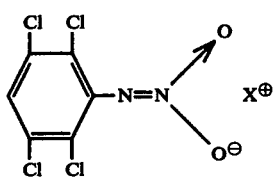

(III)

wherein the cation X represents a member selected from the group consisting of $H_3NR'$, $H_2NR'R''$, $HNR'R''R'''$ and $NR'R''R'''R''''$, and the R groups R' to R'''' each are selected from $C_1$-$C_{18}$ alkyl, aryl and benzyl; and when R' and R'' are taken together with the nitrogen they are attached to, they form a cyclic moiety selected from

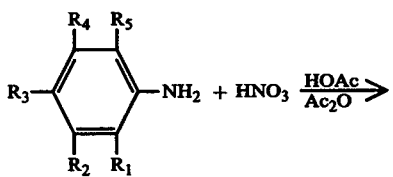

The compounds of formula (I) may be conveniently prepared from the corresponding formula (IV) substituted anilines by a variety of conventional procedures. For illustrative purposes, one such procedure is hereinbelow graphically illustrated and described, as follows:

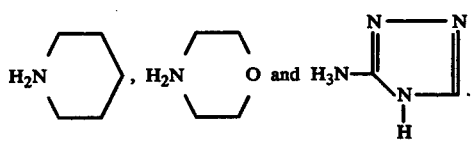

(IV)

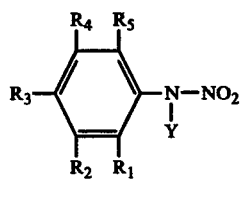

(I)

wherein $R_1$ to $R_5$ are as hereinabove defined and Y is hydrogen. The above N-nitration synthesis is conveniently carried out in a solvent, such as acetic acid, in the presence of acetic anhydride. The desired product is precipitated from the reaction mixture by the addition of ice water. Purification can be effected by conventional procedures such as recrystallization, chromatography and the like.

Certain anilines, particularly those with electron donating substituents (e.g. $CH_3$) give only low yields by the above procedure. An alternative route for these compounds consists of first treating the aniline (IV) with butyl lithium at $-80°$ to $-10°$ C.; then an alkyl nitrate, preferably methyl or ethyl nitrate. Acidification affords the nitramine I.

Formula (I) phenylnitramines, wherein $R_1$ to $R_5$ are as hereinabove described, and Y is selected from $C_1$-$C_8$ alkyl, $C_3$-$C_5$ alkenyl, $C_3$-$C_5$ alkynyl, $R_6$—O—$R_7$—,

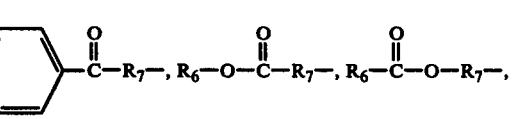

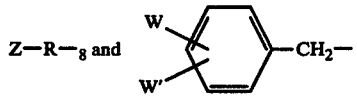

where $R_6$ is $C_1$-$C_6$ alkyl, $C_3$-$C_5$ alkenyl or $C_3$-$C_5$ alkynyl; $R_7$ is $C_1$-$C_4$ alkylene; $R_8$ is $C_2$-$C_4$ alkylene; W and W' each are hydrogen and halogen; Z is hydroxy or halogen, may be prepared by reacting the corresponding compounds of formula (I), wherein Y is hydrogen, with the appropriate organohalide (e.g. $C_1$-$C_4$ alkyl iodide, benzyl bromide and the like) in the presence of a base, such as sodium methoxide, as graphically illustrated below:

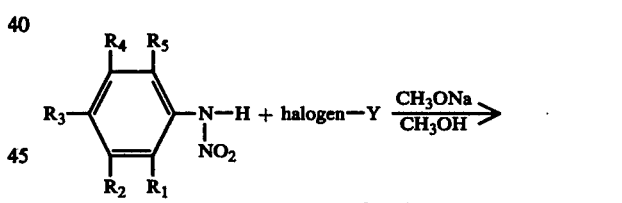

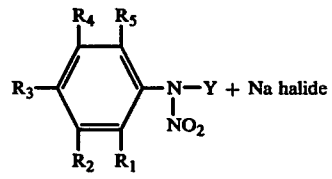

(I)

wherein $R_1$ to $R_5$ and Y are as hereinabove defined, and with the same provisos, excepting that Y cannot be hydrogen; halogen is selected from chlorine, bromine and iodine.

Formula (I) phenylnitramines, wherein $R_1$ to $R_5$ are as hereinabove described, and with the same provisos, and Y

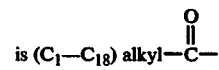

is $(C_1$—$C_{18})$ alkyl—$\overset{O}{\underset{\|}{C}}$— are conveniently obtained by preparing the $C_2$-$C_{19}$ N-acylaniline from the corresponding formula (IV) amine, followed by the hereinabove described nitration procedure.

The alkali metal salt of formula (I) phenylnitramines wherein Y is hydrogen are conveniently prepared by the addition of a metal alkoxide (e.g. sodium methoxide, potassium-t-butoxide) to a solution of the corresponding formula (I) compound in a lower alcohol (e.g. methanol). The metal salt usually precipitates out of the solution. Alternatively, the phenylnitramine may be dissolved in warm to hot water and a molar equivalent of metal hydroxide added to the solution. On cooling the mixture, the appropriate salt precipitates out. The $NH_4$ salts are prepared by the same procedures substituting ammonia for metal alkoxides and ammonium hydroxide for metal hydroxides. The above preparation of phenylnitramine salts may be graphically illustrated as follows:

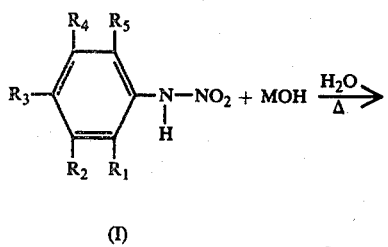

(I)

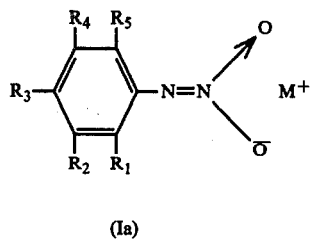

(Ia)

wherein $R_1$ to $R_5$ are as hereinabove defined; M is sodium, potassium and $NH_4$. The corresponding alkaline earth metal salts (e.g. calcium, barium) may be conveniently prepared from the formula (Ia) alkali metal salts, by dissolving same in warm to hot water and adding a stoichiometric (or slight excess) amount of an alkaline earth metal salt (e.g. $BaCl_2$), as hereinbelow graphically illustrated:

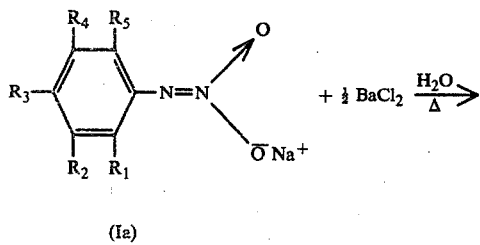

(Ia)

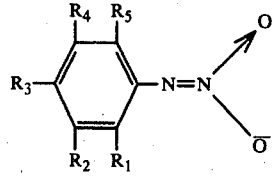

The novel organic amine salts of 2,3,5,6-tetrachlorophenylnitramine of formula (III) above, may be prepared in like manner by dissolving 2,3,5,6-tetrachlorophenylnitramine in benzene or toluene, and adding a molar equivalent (or slight excess) of the appropriate amine. Formation of the salt is rapid at room temperature (or with gentle warming) and upon cooling, the salts prepared from lower molecular weight amines usually precipitate, and are isolated by filtration. Salts formed from higher molecular weight amines (more than 8 carbon atoms in the molecule) show appreciable solubility in benzene or toluene and thus usually remain in solution. These, however, may be precipitated from solution by the addition of a lower alcohol such as methanol or ethanol.

Although benzene or toluene are preferred, other solvents, such as ether,, cyclohexanone, acetonitrile, dimethylformamide, alcohols, hydrocarbons, ethyl acetate, acetone, carbon tetrachloride and mixtures thereof may be utilized in this salt-forming reaction, if desired.

Quaternary amine salts may be prepared by titrating an aqueous methanolic solution of 2,3,5,6-tetrachlorophenylnitramine with the appropriate quaternary ammonium hydroxide using phenol red as an indicator. The resulting organic amine salts of 2,3,5,6-tetrachlorophenylnitramine, obtained by the above processes may be purified by conventional techniques such as recrystallization and precipitation.

Obviously the above described processes may also be used for the preparation of organic amine salts of other appropriately substituted formula (I) phenylnitramines, if so desired.

As stated above, the compounds of the present invention are particularly effective for the control of plant pathogenic fungi and for protecting food and fodder crops from attack by said fungi.

As used herein, the term "food and fodder crops" is meant to include field crops such as grains, forage, pasture, oil and seed crops, roots and tubers, sugar and horticultural crops such as tree fruits and citrus fruits, berries and grapes, nuts, vegetables, herbs, and specialities such as ornamentals, flowers and the like.

Among the fungicidal phenylnitramines of the present invention represented by formulae (I, II and III), a preferred group of compounds are those which show considerable activity against the rice blast pathogen (*Pyricularia oryzae* Carvara). These include: 4-trifluoromethylphenylnitramine, 2,3-dimethylphenylnitramine, 2,3,5,6-tetrachloro-4-nitrophenylnitramine, the N-acetyl derivative of 2,3,5,6-tetrachlorophenylnitramine and 2,3,5,6-tetrachlorophenylnitramine which may be in the form of the following salts:

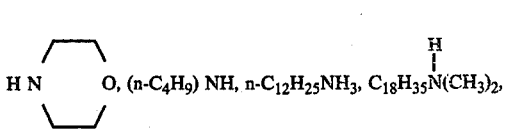

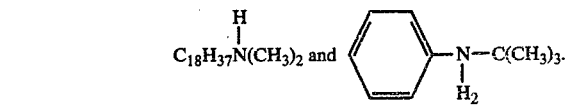

Another preferred group, active against apple scab [*Venturia inaequalis* (Cke.) Wint.] comprises 2,3-dichlorophenylnitramine, 2,4-dichlorophenylnitramine, 2,6-dichloro-4-acetamidophenylnitramine, 2,6-dibromo-4-trifluoromethylphenylnitramine, 2,4,6-tri-bromophenylnitramine, 4-methylsulfonylphenylnitramine, 2,3,5,6-tetrachloro-4-nitrophenylnitramine, the barium salt of 2,3,5,6-tetrachlorophenylnitramine, and the N-substituted derivatives of 2,3,5,6-tetrachlorophenylnitramine, wherein said substituents are —(CH(CH$_3$)$_2$ and —CH$_2$COOCH$_3$.

Formulae I and II compounds found active against apple powdery mildew [*Podosphaera leucotricha* (E&E) Salm] are 2,3-dichloro; 2,6-dichloro-; 2,6-dichloro-4-nitro-; 2,6-dimethyl-4-nitro-; 2,6-dibromo-4-methyl-; 2,6-dibromo-4-nitro-; 2,6-dibromo-4-trifluoromethyl-; 4-chloro-3-trifluoromethyl-; 3-chloro-2-trifluoromethyl-; and 3-bromophenylnitramine; also the N-acetyl derivative of 2,3,5,6-tetrachlorophenylnitramine.

Another group of formulae I, II and III phenylnitramines are found to be quite effective for the control fo barley powdery mildew (*Erysiphe graminis* f. sp. *hordei*) as listed below by substituents:

4-CF$_3$; 3-CF$_3$; 3-Br; 2,3(2,4 or 2,6)-diCl; 2-Br-4-CN; 4-Cl-2-CF$_3$; 2-Cl-5-CF$_3$; 3-Cl-2-CH$_3$; 2,6-di-Br-N-CH$_3$; 2,6-di-Br-N-C$_2$H$_5$; 2,6-di-Br-N-isopropyl; 2,6-diBr-N-benzyl; 2,6-diBr-4-CN; 2,6-diCl-4-NO$_2$; 2,6-diBr-4-CH$_3$; 2,6-di-Br-N-CH$_2$OCH$_3$; 2,6-diCl-4-CH$_3$CONH-; 2,67-diCl-4-C$_2$H$_5$CONH-; 2,6-diCH$_3$; 2,6-diCH$_3$-4-NO$_2$; 2,6-di-C$_2$H$_5$; 2,4,6-triBr; 2,3,4,5-tetra-Cl; 2,3,4,5-tetra-Cl-NH$_4$ salt; 2-NO$_2$; 4-CH$_3$S-; 4-CH$_3$SO$_2$-; 2-NO$_2$-4-CF$_3$; 2,4-diNO$_2$; 2,3,5,6-tetra-Cl and its Ba salt; and 2,3,5,6-tetra-Cl-substituted on the nitramine N with:

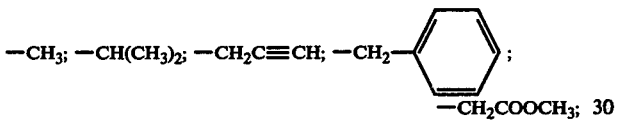

—CH$_3$; —CH(CH$_3$)$_2$; —CH$_2$C≡CH; —CH$_2$—

—CH$_2$COOCH$_3$;

and acetyl; and the N-tert-butylaniline salt of 2,3,5,6-tetrachlorophenylnitramine.

As stated above, the compounds of the present invention represented by formulae I and II are particularly (and selectively) effective for the control of fungi and for protecting food and fodder crops from attack by said fungi.

In practice, the active compounds are generally formulated as dusts, dust concentrates, wettable powders, emulsion concentrates, flowable concentrates and the like.

Dusts can be prepared by grinding about 1% to 15% by weight of the active compound with about 99% to 85% by weight of an inert diluent such as attaclay, diatomaceous earth, kaolin, pumic, talc and the like.

Dust concentrates are made in a similar fashion excepting that percent by weight of active ingredient is increased to about 16% to 75% of the composition.

Wettable powders may be prepared in the same manner as dust concentrates, but usually contain, in addition to the active ingredient and solid diluent, from about 1% to 5% by weight of a wetting agent such as sodium isopropylnaphthalene sulfonate or the sodium salt of a sulfonated naphthalene formaldehyde condensate, and from about 1% to 5% by weight of a dispersing agent such as hydroxyethyl cellulose. A typical formulation would be 50% by weight of active ingredient, 2% of dispersing agent, 5% of wetting agent and 43% attapulgite.

Emulsion concentrates may be prepared by dissolving 15% to 70% by weight of the compound in 85% to 30% of a solvent such as benzene, toluene, xylene, kerosene, 2-methoxy ethanol, propylene glycol, diethylene glycol, diethylene glycol monomethyl ether, formamide, methyl formamide and the like and mixtures thereof. Advantageously, surfactants such as polyoxyethylated vegetable oil or an alkyl phenoxy polyoxyethylene ethanol are also incorporated in amounts of 1% to 5% by weight of said concentrate.

In using wettable powders or emulsion concentrates, the formulated material is generally dispersed in water and applied as a liquid spray to the above-said crops, which are to be protected from attack by fungi. Usually the sprays contain 10 ppm to 2000 ppm and preferably 50 ppm to 1000 ppm active compound and the crops to be protected are sprayed to run-off with said dilute fungicidal spray.

The invention is further illustrated by the following examples which are not limitative thereof.

EXAMPLE 1

General Procedures for the Preparation of Phenylnitramines

Procedure A

To a cooled (10° C. to 20° C.) solution containing an appropriately substituted aniline (0.10 mole) in glacial acetic acid (100 to 500 ml) is added dropwise, with cooling and stirring during 15 to 30 minutes, 90% nitric acid (15 to 16 ml; 0.28–0.30 mole). In many reactions, the nitrate salt precipitates out. After 15 minutes to 1 hour, acetic anhydride (15 ml) is added dropwise with stirring and the temperature allowed to reach 18° C. to 25° C. The reaction mixture darkens and becomes homogeneous, at which point the mixture is poured into ice water (1:1, 1 liter). The resulting precipitate is filtered, washed with water and dissolved in aqueous 10% sodium carbonate.

The acidic filtrate is extracted with chloroform (2 × 200 ml) and the chloroform layer is washed with water (2 × 200 ml). The chloroform layer is extracted with 10% aqueous sodium carbonate and both of the above carbonate solutions are combined, washed with chloroform, cooled to 10° C. and acidified with ice cold 2N hydrochloric acid to precipitate the phenylnitramine product. The nitramine is filtered, washed with cold water, dried in vacuo and recrystallized from the appropriate solvent.

If desired, the above chloroform solution may be evaporated to dryness to afford a mixture of the desired product, the unreacted aniline and side products. The impurities may be separated by conventional procedures, such as selective crystallization, extraction, chromatography and the like.

Various substituted phenylnitramine prepared by the above general procedure are set forth in Table I below.

An alternative procedure (B) is described below for certain anilines containing electron donor substituents.

Procedure B

Preparation of 2,6-dimethylphenylnitramine

To a well stirred solution of 2,6-dimethylaniline (12.1 g, 0.1 mole) in dry ether (200 ml), under a nitrogen atmosphere, a 2% n-butyllithium solution (25 ml) is added over 1 hour while the reaction mixture is kept at −50° C. with dry ice. A solid separates. The reaction mixture is allowed to warm up to −10° C. and is then recooled to −50° C. A solution of ethyl nitrate (9.1 g, 0.1 mole) in ether (50 ml) is added slowly with stirring over 20 minutes. On completion of the addition the reaction mixture is allowed to warm up. At −25° C. the mixture becomes homogeneous and at −18° C. a copius precipitate forms. The mixture is then allowed to stand under nitrogen at 20° C. for 16 hours. The solid is filtered off (it appears to be hygroscropic) and is dissolved in ice water (100 ml). The solution is carefully acidified with ice cold 1N hydrochloric acid to afford 9.0 g (69% yield) of title product; m.p. 104.5°–105° C. Recrystallization from hexane affords almost white crystals; m.p. 105.5°–106° C.

Analysis calculated for $C_{20}H_{17}N_3O_2Cl_4$: C, 50.76; H, 3.62; N, 8.88. Found: C, 51.07; H, 3.74; N, 8.39.

EXAMPLE 4

Preparation of the N,N-dimethylaniline salt of 2,3,5,6-tetrachloro-N-nitroaniline

Table I

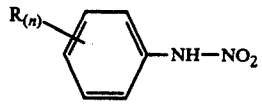

| $R_{(n)}$ | Melting Point °C | Crystallization Solvent | % Yield |
|---|---|---|---|
| 2,4-di-$NO_2$ | 80–82 (dec) | benzene/hexane | 57 |
| 4-CN | 155–156 (dec) | toluene | 25 |
| 4-$CF_3$ | 71–72 | heptane or water | 58 |
| 2-I | 92–94 (dec) | hexane | 27 |
| 4-Cl | 82 | hexane | 3 |
| 3-$CF_3$ | 66–66.5 | hexane | 40 |
| 2,4,6-tri-Br | 138–139 (dec) | cyclohexane | 38 |
| 2,3-di-Cl | 58–60 | hexane | 83 |
| 2,4-di-Cl | 55–56 | hexane | 58 |
| 2,6-di-Cl | 102–103 (dec) | water | 69 |
| 3,5-di-Cl | 120–122 (dec) | hexane | 63 |
| 4-$SO_2CH_3$ | 172–174 (dec) | methanol | 38 |
| 2 or (3)-$NO_2$-4-$SCH_3$ | 98–99.5 (dec) | cyclohexane | 3 |
| 2,6-di-Br-4-CN | 142 (dec) | ethanol-water | 21 |
| 2-Br-4-CN | 128.5–129.5 (dec) | benzene-light petroleum bp. 30–60° C | 56 |
| 3-Br | 96–98 (dec) | none | 4 |
| 2,3,5,6-tetra-Cl | 144–146 (dec) | cyclohexane | 84 |
| 2,6-di-$CH_3$-4-$NO_2$ | | | |
| 2,6-di-Br-4-$CF_3$ | 110–11 (dec) | hexane | 80 |
| 4-Cl-3-$CF_3$ | 94–95 | cyclohexane | 21 |
| 2-Cl-5-$CF_3$ | 50–51 | cyclohexane | 51 |
| 2-$NO_2$-4-$CF_3$ | 48–50 | hexane | 25 |
| 2,6-di-Br-4-$CH_3$ | 120–121 (dec) | hexane | 41 |
| 3-Cl-2-$CH_3$ | 93.5–94 (dec) | hexane | 2 |
| 2,6-di-$CH_3$* | 104.5–105 | hexane | 69 |
| 4-$CH_3CONH$-2,6-di-Cl | 165 (dec) | none | 79 |
| 2,3-di-$CH_3$ | 69–76 | hexane | 29 |
| 4-$NO_2$-2,3,5,6-tetra-Cl | 83 (dec) | — | |
| 2,3,4,5-tetra-Cl | 139–140 | carbon tetrachloride | 32 |
| 2,6-di-Cl-4-$C_2H_5CONH$— | 135–136 | — | — |
| 2,6-di-Cl-4-$(CH_3)_2CHOOC$—NH— | 121–122 dec | — | 38 |
| 2,3,5,6-tetramethyl* | 119–119.5 | — | 99.6 |

*Procedure B

EXAMPLE 2

Preparation of 2,3,5,6-tetrachlorophenylnitramine N-barium salt

To an aqueous solution of sodium carbonate (5.1 g; 0.95 mole) in water (500 ml) is added 2,3,5,6-tetrachlorophenylnitramine (13.75 g; 0.05 mole). The mixture is warmed to 100° C. and an almost clear solution is obtained. The solution is rapidly filtered hot and poured into a boiling solution of barium chloride (30.0 g) in water (500 ml). A precipitate is formed immediately. An additional liter of boiling water is added and the resulting mixture is filtered hot. On cooling, the title product separates out in the form of white crystals, m.p. 288° C. to 289° C. The product yield is 11.9 g (65%).

EXAMPLE 3

Preparation of the dibenzylamine salt of 2,3,5,6-tetrachloro-N-nitroaniline

Dibenzylamine (10.0 g; 0.051 mole) in ether (50 ml) is added to a solution of 2,3,5,6-tetrachloro-N-nitroaniline (9.0 g; 0.0326 mole) in methanol (60 ml). Immediately, a flocculent white precipitate forms. The precipitate is isolated by filtration, washed with ether and dried to afford 12.3 g (100%) title product, m.p. 178.5° C. to 179° C. (dec.)

A solution of N,N-dimethylaniline (1.69 g; 0.014 mole) in benzene (24 ml) is added with stirring to a warm (30° C. to 40° C.) solution of 2,3,5,6-tetrachloro-N-nitroaniline (3.86 g; 0.014 mole) in benzene (24 ml). After warming for 5 minutes at 50° C. the solution is cooled but no solid separates. The benzene is evaporated and the residue recrystallized from methanol to afford 4.5 g of title product, m.p. 135° C. (dec).

Analysis calculated for $C_{14}H_{13}N_3O_2Cl_4$: C, 42.35; H, 3.30; N, 10.58. Found: C, 42.37; H, 3.31; N, 10.58.

EXAMPLE 5

Preparation of the ethanolamine salt of 2,3,5,6-tetrachloro-N-nitroaniline

A solution of ethanolamine (2.3 g; 0.0377 mole) in acetonitrile (10 ml) and toluene (40 ml) is added dropwise with stirring to a solution of 2,3,5,6-tetrachloro-N-nitroaniline (10.4 g; 0.0377 mole) in toluene (150 ml). Instantly a copious precipitate forms. The reaction mixture is diluted with toluene (300 ml) and after 30 minutes the precipitate is isolated by filtration, washed with toluene and dried to afford 12.3 g (97%) of the title product, m.p. 164° C. to 165° C.

Analysis calculated for $C_8H_9N_3O_3Cl_4$: C, 28.51; H, 2.69; N, 12.47. Found: C, 28.31; H, 2.41; N, 12.49.

EXAMPLE 6

Preparation of novel salts of 2,3,5,6-tetrachloro-N-nitroaniline

By the procedure of Examples 2 and 5 the following novel salts of 2,3,5,6-tetrachloro-N-nitroaniline are prepared as listed in Table II below. The melting points (uncorrected) of said salts are determined on a Thomas Hoover Capillary Melting Point Apparatus; while the thermal decomposition points of said salts are determined on a Dupont 900 Differential Thermal Analyzer. Rate of heating: 20° C./min; analyzer calibrated in the range of 81° C. to 193° C. Decompositions are recorded by an exothermic response and the temperatures given in Table II below are assessed by the "onset method".

Table II $$\left[\begin{array}{c}\text{2,3,5,6-tetrachlorophenyl-N=N}\diagup\!\!\diagdown\!\!\text{O}\\\text{O}\end{array}\right]\cdot X^+$$

| X | Melting Point (° C) | Thermal Decomposition Point (° C) | δ 4-H of Phenyl (ppm) | δ 4-C of Phenyl (ppm) |
|---|---|---|---|---|
| Na (1.5 H$_2$O) | 299 (dec) | — | — | — |
| Ba ½ (2H$_2$O) | 288–289 (dec) | — | — | — |
| K | 295–296 (dec) | 272 | 2.35 (DMSO) | 124.7 |
| NH$_3$CH$_3$ | 182–183 | 183 | — | — |
| NH$_2$(CH$_3$)$_2$ | 158–159 | 167 and 176 | — | — |
| NH(CH$_3$)$_3$ | 156–156.5 | — | — | — |
| NH(C$_2$H$_5$)$_3$ | 164–165 | 169 | 2.61 | — |
| NH$_2$(C$_3$H$_7$)$_2$ | 191–192 | 204 | 2.62 | — |
| NH(C$_3$H$_7$)$_3$ | 121–122 | 154 | — | — |
| NH$_2$(C$_4$H$_9$)$_2$ | 194–195 | 207 | 2.63 | — |
| NH(C$_4$H$_9$)$_3$ | 97–98 and 114–115 | — | — | — |
| NH$_4$ | 178–179 | 178 | — | — |
| NH$_2$(CH$_2$CH$_2$OH)$_2$ | 147.5–148 | 173 and 177 | — | — |
| NH$_2$(CH$_2$—C$_6$H$_5$)$_2$ | 178.5–179 | 183 | — | — |
| H$_2$N-morpholine | 163–164 | 176 | 2.50 | 127.82 |
| NH$_3$CH$_2$CH$_2$NH$_2$ | 208–209 | 208 | — | — |
| NH$_3$-(2,6-dimethylphenyl) | 134.5–136 | 143 | — | — |
| C$_4$H$_9$-t-NH$_2$-phenyl | 163 | 163 | — | — |
| NH$_3$-phenyl | 143–145 | 138 | — | — |
| NH$_3$CH$_2$CH$_2$OH | 164–165 | 203 | 2.34 (DMSO) | — |
| NH$_3$C$_8$H$_{17}$ | 103–103.5 | 163 | — | — |
| NH$_3$-imidazole | 165–166 | 173 | — | — |
| NH(CH$_2$CH$_2$OH)$_3$ | 128–130 | 150 | 2.56 | — |
| NH$_3$(CH$_2$)$_3$NHC$_{12}$H$_{25}$-n | 178–181 | 184 | 2.66 | — |
| NH(CH$_3$)$_2$ · C$_6$H$_5$ | 95–96 | 128 | 2.55 | — |
| NH$_3$C$_{16}$H$_{33}$ | 103–104 | 148.5 | 2.59 (DMSO) | — |
| NH$_3$(CH$_2$)$_3$NH(CH$_2$)$_8$CH=CHC$_8$H$_{17}$-n | 94–103 | 183.5 | 2.62 | — |
| NH$_2$(C$_{18}$H$_{37}$)$_2$ | 165–170 | 168 | 2.65 | — |
| NHC$_{18}$H$_{37}$ · (CH$_2$CH$_2$O)$_2$H · (CH$_2$CH$_2$O)$_3$H | syrup | 153–157 | 2.69 | — |
| NH$_3$C$_{12}$H$_{25}$-n | 104–105 | 166 | — | — |
| NH(CH$_2$CH$_2$OH)$_2$ · (CH$_2$)$_3$NC$_{18}$H$_{37}$ | syrup | — | — | — |
| H$_2$N-cyclohexyl | 165 | 203 | 2.57 | — |
| NH$_3$C$_{18}$H$_{37}$-n | 90.5–93 | 140 and 199 | 2.53 | — |
| NH$_3$(CH$_2$)$_3$NHC$_{18}$H$_{37}$-n | 157.5–158.5 | 160 and 196 | — | — |
| NH(CH$_2$CH$_2$OH)$_2$ · C$_{18}$H$_{37}$-n | syrup | 141 and 193 | — | — |
| NH(CH$_3$)$_2$ · C$_{18}$H$_{37}$-n | 85–86 | 147 and 200 | 2.61 | — |
| NH$_3$C$_{12}$H$_{25}$(CH$_2$)$_3$CO$_2$H | 99.5–101 | 116 and 170 | 2.55 | — |
| NH$_3$(CH$_2$)$_8$CH=CH(CH$_2$)$_7$CH$_3$ | -80 | 157 (slight) | 2.57 | — |

Table II-continued

[Structure: 2,3,5,6-tetrachlorophenyl-N=N with N bonded to two O (one O⁻, one O with arrow), bracketed with .X⁺]

| X | Melting Point (° C) | Thermal Decomposition Point (° C) | δ 4-H of Phenyl (ppm) | δ 4-C of Phenyl (ppm) |
|---|---|---|---|---|
| NH₃CH₂CH₂OC₂H₅ | 143–145 | 154 and 167 | — | — |
| Si ¼ (8 H₂O) | 299 | — | 2.35 (DMSO) | — |
| Parent Compound [2,3,5,6-tetrachloro-NH—NO₂ aniline] | 144–145 | 150 | 2.27 or (1.24) (DMSO) | 132.38 | dec = decomposed

The above table shows the proton nmr chemical shift of the 4-H proton of the phenyl ring. In deuterochloroform, a signal range of δ2.4–2.65 is observed for all salts, and in deutero dimethylsulfoxide: 2.34–2.59 range; whereas 2,3,5,6-tetrachloro-N-nitroaniline shows a chemical shift of 2.25 in CDCl₃ and 1.24 in DMSO.

The $C_{13}$ nmr was run on a CFT-20 nmr spectrometer. The chemical shift of the 4-C of the phenyl ring is in the range of 124.4–127.8, whereas the parent 2,3,5,6-tetrachloro-N-nitroaniline 4-C chemical shift is 132.38 ppm.

EXAMPLE 7

General Procedures for the Preparation of N-substituted phenylnitramines

To the appropriately substituted phenylnitramine (0.01 mole) in absolute methanol (50 ml) is added sodium methoxide (1.1 g; 0.020 mole) and the mixture warmed until complete solution is achieved. After cooling, the appropriate alkyl halide (e.g. iodide) is added to the solution, preferably in a 2 to 5 molar excess and the reaction mixture heated at reflux for 3 hours.

The reaction mixture is then cooled and poured into ice water made alkaline with 10% aqueous sodium carbonate, and is filtered to yield the desired product in the form of a solid. If desired, the product may be purified by standard laboratory procedures, such as recrystallization, chromatography and the like.

The desired N-acetyl phenylnitramines can be prepared by acetylating the appropriately substituted anilines, and then nitrating same by the procedure of Example 1.

By the above procedure, the following compounds are prepared:

| Structure | m.p. (° C) |
|---|---|
| 2,3,5,6-tetrachlorophenyl-N(NO₂)—CH(CH₃)₂ | 63–64 |
| 2,3,5,6-tetrachlorophenyl-N(NO₂)—CH₂—C≡CH | 102–103 |
| 2,3,5,6-tetrachlorophenyl-N(NO₂)—CH₂—C₆H₅ | 103–103.5 |
| 2,3,5,6-tetrachlorophenyl-N(NO₂)—C(O)—CH₃ | 133–134 |
| 2,3,5,6-tetrachlorophenyl-N(NO₂)—CH₂—CH=CH₂ | 60–60.5 |
| 2,6-dibromo-3,5-dichlorophenyl-N(NO₂)—CH₃ | 128–129 |
| 2,3,5,6-tetrachlorophenyl-N(NO₂)—C₈H₁₇ | 49–50 |

-continued

| Structure | m.p. (° C) |
|---|---|
| 2,6-dibromo-N-ethyl nitramine | 69–69.5 |
| 2,6-dibromo-N-benzyl nitramine | 85–86 |
| 2,6-dibromo-N-isopropyl nitramine | 67–68 |
| 2,6-dibromo-N-methoxymethyl nitramine | 64.5–67 |
| 2,6-dimethyl-3,5-dinitro-N-(sec-butyl) nitramine | |
| 2,3,5,6-tetrachloro-N-methyl nitramine | 134–135.5 |
| 2,3,5,6-tetrachloro-N-CH₂CO₂CH₃ nitramine | 94–95 |
| 2,3,5,6-tetrachloro-N-CH(CH₃)CO₂C₂H₅ nitramine | 109–110 |
| 2,3,5,6-tetrachloro-N-CH₂CH₂Br nitramine | 94–95 |
| 2,3,5,6-tetrachloro-N-CH₂CH₂OH nitramine | 160–161 |

-continued

| Structure | m.p. (° C) |
|---|---|
| 2,3,5,6-tetrachloro-N-C₂H₅ nitramine | 124–125 |
| 2,3,5,6-tetrachloro-N-CH₂CH₂OSO₂CH₃ nitramine | 134–135 |
| 2,3,5,6-tetrachloro-N-CH₂CH₂OC(O)CH₃ nitramine | 89.5–90 |
| 2,3,5,6-tetrachloro-N-CH₂CH₂Cl nitramine | 95–96 |
| 2,3,5,6-tetrachloro-N-CH₂OCH₂C≡CH nitramine | 90.5–91 |
| 2,3,5,6-tetrachloro-N-CH₂OCH₂SCH₂CO₂C₂H₅ nitramine | 90.5–91 |
| 2,3,5,6-tetrachloro-N-CH₂SCH₂CO₂C₂H₅ nitramine | 77–79 |
| 2,3,5,6-tetrachloro-N-CH₂OCH(CH₃)₂ nitramine | 108–109 |
| 2,3,5,6-tetrachloro-N-CH₂CH₂—OCH₃ nitramine | 144–145 |

EXAMPLE 8

Preparation of the tetramethylammonium salt of 2,3,5,6-tetrachlorophenylnitramine A solution of 2,3,5,6-tetrachlorophenylnitramine (2.0 g) in methanol is titrated with a 20% methanolic solution of tetramethylammonium hydroxide (3.3 g solution, containing 0.66 g of the ammonium compound) using phenol red as an indicator. The methanol is recovered at 40° C. at 25 mm pressure. A pink crystalline solid weighing 2.67 g is obtained. m.p. 228°–229° C. (dec). The solid is recrystallized from benzene and ethanol; m.p. 221°–222° C. (with darkening beginning at 219° C.).

Analysis Calculated: C, 34.41; H, 3.75; N, 12.04; Cl, 40.63. Found: C, 34.40; H, 3.77; N, 12.06; Cl, 40.52.

EXAMPLE 9

Preparation of the benzyltriethylammonium salt of 2,3,5,6-tetrachlorophenylnitramine Benzyltriethylammonium chloride (2.5 g) is converted to the hydroxide with ion exchange resin AN-QA-542. The aqueous solution is concentrated to about 40 ml. The 2,3,5,6-tetrachlorophenylnitramine (2.5 g) is dissolved in methanol (ca 75 ml) and the benzyltriethylammonium hydroxide is added dropwise using phenol red as an indicator, to a faint purple end product. The solvent is then removed at 40° C. and 20 mm pressure to yield a thick syrup. The syrup is azeotroped with benzene and crystallization is initiated by scratching the sides of the vessel. There is obtained 3.7 g of title product; m.p. 126°–128° C.; tinted with the indicator. The product is dissolved in a water/methanol mixture and the solution decolorized with activated carbon. The solvents are removed and the residue dried; m.p. 127°–218° C.

Analysis Calculated: C, 48.84; H, 4.96; N, 8.99; Cl, 30.35. Found: C, 49.83; H, 5.29; N, 8.81; Cl, 29.35.

EXAMPLE 10

Evaluation of the foliar fungicidal activity of various phenylnitramines

To determine the effectiveness of phenylnitramines as foliar fungicidal agents, a variety of pathogenic fungi, host plants and test compounds are used in the following tests. Pathogens, host plants, the method of testing and the rating system used are reported below along with the data obtained.

| Disease Common Name | Causal Agent |
|---|---|
| Rice Blast | *Pyricularia oryzae* Carvara |
| Apple Scab | *Venturia inaequalis* (Cke.) Wint |
| Barley Powdery Mildew | *Erysiphe graminis* DC f.sp.*hordei* Em. Marchal |
| Apple Powdery Mildew | *Podosphaera leucotricha* (E&E) Salm. |

| Host Plants | |
|---|---|
| Rice | (*Oryza sativa*) (Cv. Nato) |
| Apple | (*Malus sylvestris*) (Seedling) |
| Barley | (*Hordeum vulgare* L.) (Cv. Larker) |

Plants are individually grown in 5 cm peat squares and assembled in 7.62 cm × 25.4 cm pressed fibre flats the week prior to spraying. Several plants/peat square of rice and barley are used, while a single apple seedling is used for the apple diseases. A separate container is used for those plants in the mildew evaluation. The complete test system is shown below:

| | Series I | | Series II |
|---|---|---|---|
| Rice: | Rice blast | Apple: | Powdery mildew |
| Apple: | Apple scab | Barley: | Powdery mildew |

Spray solutions are prepared in the final concentrations given in the tables below in 50 ml of 50% aqueous acetone. In all cases acetone is added first to solubilize the compound and solutions made to final volume with deionized water.

Two containers, one from Series I and one from Series II (see above), are sprayed simultaneously on a turntable with 50 ml of the test solution. Spray is provided by two fixed Spray System Co. nozzles mounted to deliver vertical and horizontal solid cone patterns. Immediately thereafter, all plants are returned to the greenhouse to permit the deposit to dry.

Plants in Series I and II are separately inoculated. Plants in Series I are inoculated with aqueous conidial suspensions of the respective pathogens using a Devilbiss paint sprayer operated at 0.28 to 0.42 kg/cm$^2$ pressure and are transferred to a controlled temperature/humidity cabinet (ambient temperature; RH 95%). Plants in Series II are dusted with respective powdery mildew conidia and then removed to the greenhouse to await disease development. All plants are rated for disease severity on a scale of 1–7 (clean-kill) as described below:

| Rating | Disease Description | Disease Percentage Range | Midpoint |
|---|---|---|---|
| 1 | Nil | 0 | 0 |
| 2 | Trace disease | 0–8.4 | 4.2 |
| 3 | Slight disease | 8.5–21.4 | 14.9 |
| 4 | Moderate disease | 21.5–78.6 | 50.0 |
| 5 | Heavy disease | 78.7–91.6 | 85.1 |
| 6 | Severe disease | 91.7–99.9 | 95.8 |
| 7 | Plant Kill | 100 | 100 |

In the accompanying Tables (III to VI), results are reported as percent disease control. Disease severity scores are converted to estimated disease percentages from tables, similar to those published by Eli Lilly and Co. (Elanco) for the 12-point Barrett and Horsefall rating scale. Disease percentage of treatments vs controls are then converted to percent disease control according to the formula:

$$\frac{\text{Disease incidence control (\%)} - \text{Disease incidence treatment (\%)}}{\text{Disease incidence control (\%)}} \times 100 = \text{Percent Disease Control}$$

TABLE III

Evaluation of Foliar Fungicidal Activity of Substituted Phenylnitramines for the Control of Rice Blast (*Pyricularia oryzae* Carvara), Expressed as Percent Disease Control

| Compound | Rate of Application (ppm) | Rice Blast Percent Disease Control |
|---|---|---|
| CF$_3$—⟨phenyl⟩—NH—NO$_2$ | 500 | 84 |
| Cl,Cl,Cl,Cl-phenyl—N=N(O)(O$^-$) ⟨phenyl⟩—N$^+$C(CH$_3$)$_3$H$_2$ | 500 | 84 |

TABLE III-continued
Evaluation of Foliar Fungicidal Activity of Substituted Phenylnitramines for the Control of Rice Blast (*Pyricularia oryzae Carvara*), Expressed as Percent Disease Control

| Compound | Rate of Application (ppm) | Rice Blast Percent Disease Control |
|---|---|---|
| 2,3-dimethylphenyl-NH-NO$_2$ | 500 | 81 |
| 2,3,5,6-tetrachloro-4-nitro-phenyl-NH-NO$_2$ | 500 | 86 |
| 2,3,5,6-tetrachlorophenyl-N(NO$_2$)-C(=O)-CH$_3$ | 500 | 100 |
| pentachlorophenyl-N=N(O)(O$^-$) · H$_2$N$^+$-morpholine | 1000 | 83 (M/Sv) |
| pentachlorophenyl-N=N(O)(O$^-$) · C$_{18}$H$_{35}$-N$^+$H(CH$_3$)$_2$ | 1000 | 83 (M/Sv) |
| pentachlorophenyl-N=N(O)(O$^-$) · (n-C$_4$H$_9$)$_3$N$^+$H | 1000 | 83 (M) |
| pentachlorophenyl-N=N(O)(O$^-$) · n-C$_{12}$H$_{25}$-N$^+$H$_3$ | 1000 | 83 (Sl) |
| pentachlorophenyl-N=N(O)(O$^-$) · C$_{18}$H$_{37}$-N$^+$H(CH$_3$)$_2$ | 1000 | 69 (M) |

Sl = Slight phytotoxicity
M = Moderate phytotoxicity
Sv = Severe phytotoxicity

TABLE IV
Evaluation of Foliar Fungicidal Activity of Substituted Phenylnitramines for the Control of Apple Scab [*Venturia inaequalis* (Cke) Wint.] Expressed as Percent Disease Control

| Compound | Rate of Application (ppm) | Apple Scab Percent Disease Control |
|---|---|---|
| 2,4,6-tribromophenyl-NH-NO$_2$ | 500 | 75 (M) |
| 2,3-dichlorophenyl-NH-NO$_2$ | 500 / 200 | 76 / 67 |
| 2-chlorophenyl-NH-NO$_2$ | 500 | 93 |
| 4-(CH$_3$SO$_2$)phenyl-NH-NO$_2$ | 500 | 76 |
| 2,6-dibromo-4-CF$_3$-phenyl-NH-NO$_2$ | 500 | 76 |
| 4-(CH$_3$-CO-NH)-2,6-dichlorophenyl-NH-NO$_2$ | 500 | 76 |
| pentachlorophenyl-N=N(O)(O$^-$) Ba$^{2+}$ | 500 | 76 |
| pentachlorophenyl-N=N(O$^-$)-O-CH(CH$_3$)$_2$ and pentachlorophenyl-N(NO$_2$)-CH(CH$_3$)$_2$ | 500 | 76 |
| 4-O$_2$N-2,3,5,6-tetrachlorophenyl-NH-NO$_2$ | 500 | 81 |

TABLE IV-continued
Evaluation of Foliar Fungicidal Activity of Substituted Phenylnitramines for the Control of Apple Scab [*Venturia inaequalis* (Cke) Wint.] Expressed as Percent Disease Control

| Compound | Rate of Application (ppm) | Apple Scab Percent Disease Control |
|---|---|---|
| 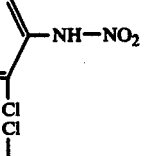 | 500 | 96 |
|  | 200 | 83 |

Sl = Slight phytotoxicity
M = Moderate phytotoxicity
Sv = Severe phytotoxicity

TABLE V
Evaluation of Foliar Fungicidal Activity of Substituted Phenylnitramines for the Control of Apple Powdery Mildew [*Podosphaera leucotricha* (E&E) Salm.], Expressed as Percent Disease Control

| Compound | Rate of Application (ppm) | Apple Powdery Mildew Percent Disease Control |
|---|---|---|
| 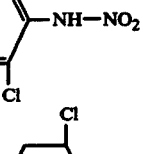 | 500 | 96 (Sl) |
| 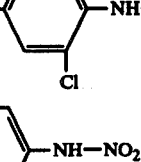 | 500 | 84 (Sv) |
| 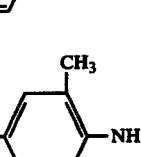 | 500 | 84 (M) |
| 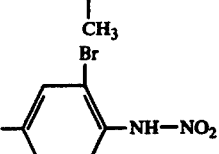 | 500 | 84 |
| 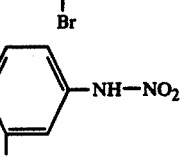 | 500 | 84 |
| 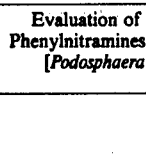 | 500 | 84 (SV) |
| 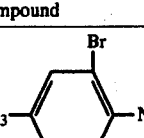 | 500 | 84 (SV) |

TABLE V-continued
Evaluation of Foliar Fungicidal Activity of Substituted Phenylnitramines for the Control of Apple Powdery Mildew [*Podosphaera leucotricha* (E&E) Salm.], Expressed as Percent Disease Control

| Compound | Rate of Application (ppm) | Apple Powdery Mildew Percent Disease Control |
|---|---|---|
| 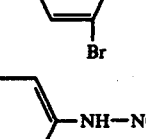 | 500 | 84 |
| 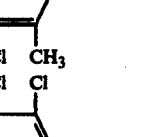 | 500 | 84 |
| 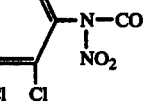 | 500 | 92 (Sl) |

Sl = Slight phytotoxicity
M = Moderate phytotoxicity
Sv = Severe phytotoxicity

TABLE VI
Evaluation of Foliar Fungicidal Activity of Substituted Phenylnitramines for the Control of Barley Powdery Mildew (*Erysiphe graminis* f. sp. *hordei*), Expressed as Percent Disease Control

| Compound | Rate of Application (ppm) | Barley Powdery Mildew Percent Disease Control |
|---|---|---|
| CF$_3$—⌬—NH—NO$_2$ | 500 | 96 (M) |
|  | 200 | 91 |
|  | 100 | 95 |
|  | 50 | 84 |
| ⌬(CF$_3$)—NH—NO$_2$ | 500 | 96 |
| Br—⌬(Br)(Br)—NH—NO$_2$ | 500 | 100 (M) |
|  | 200 | 84 |
|  | 100 | 70 |
|  | 50 | 70 |
| [Cl$_2$C$_6$H$_3$—N=N—O$_2$]⁻ · ⌬—CH$_2$—N⁺(C$_2$H$_5$)$_3$ | 500 | 84 |
|  | 200 | 71 |
|  | 100 | 48 |
|  | 50 | 48 |
| ⌬(ClCl)—NH—NO$_2$ | 500 | 100 (Sl) |
| Cl—⌬(Cl)—NH—NO$_2$ | 500 | 100 |

TABLE VI-continued
Evaluation of Foliar Fungicidal Activity of Substituted Phenylnitramines for the Control of Barley Powdery Mildew (*Erysiphe graminis* f. sp. *hordei*), Expressed as Percent Disease Control

| Compound | Rate of Application (ppm) | Barley Powdery Mildew Percent Disease Control |
|---|---|---|
| 2,6-diCl-C6H3-NH-NO2 | 500 | 100 |
| 3,5-diCl-C6H3-NH-NO2 | 500 | 100 (M) |
| CH3-SO2-C6H4-NH-NO2 | 500 | 100 |
| CH3S-, NO2- C6H3-NH-NO2 (or isomer CH3S-, NO2-) | 500 | 100 |
| 2,6-diBr-4-NC-C6H2-NH-NO2 | 500 | 84 |
| 2-Br-4-NC-C6H3-NH-NO2 | 500 | 100 |
| 2-Cl-4-O2N-C6H3-NH-NO2 | 500 | 100 (M) |
| 3-Br-C6H4-NH-NO2 | 500 | 96 |
| 2,3,5,6-tetraCl-C6H-NH-NO2 | 200 | 100 |
|  | 100 | 95 |
|  | 50 | 95 |
| 2,6-diCH3-4-O2N-C6H2-NH-NO2 | 500 | 100 |
| 2,6-diBr-4-CF3-C6H2-NH-NO2 | 500 | 100 (SI) |
|  | 200 | 83 |
| 3-Cl-5-CF3-C6H3-NH-NO2 | 500 | 100 (Sv) |
| 2-CF3-6-Cl-C6H3-NH-NO2 | 500 | 100 (M) |
| 4-CF3-2-NO2-C6H3-NH-NO2 | 500 | 96 |
| 2,6-diBr-4-CH3-C6H2-NH-NO2 | 500 | 100 |
| 2,6-diCl-4-(CH3-CO-NH)-C6H2-NH-NO2 | 500 | 84 |
| 2,6-diCl-4-(C2H5CO-NH)-C6H2-NH-NO2 | 500 | 100 (SI) |
| 2,6-diC2H5-C6H3-NH-NO2 | 500 | 100 |
| 2,3,5,6-tetraCl-C6H-N(Ba)-NO | 500 | 100 |
| 2,6-diBr-C6H3-N(CH3)-NO2 | 500 | 89 |
| 2,6-diCl-4-(C2H5CONH)-C6H2-NH-NO2 | 500 | 89 |
| 2,6-diCl-4-((CH3)2CHOOC-HN)-C6H2-NH-NO2 | 200 | 97 |
| 2,6-diBr-C6H3-N(C2H5)-NO2 | 500 | 89 |
| 2,6-diBr-C6H3-N(CH2C6H5)-NO2 | 500 | 100 |

TABLE VI-continued

Evaluation of Foliar Fungicidal Activity of Substituted Phenylnitramines for the Control of Barley Powdery Mildew (*Erysiphe graminis* f. sp. *hordei*), Expressed as Percent Disease Control

| Compound | Rate of Application (ppm) | Barley Powdery Mildew Percent Disease Control |
|---|---|---|
| 2,6-Br₂-C₆H₃-N(CH(CH₃)₂)-NO₂ | 500 | 100 |
| 2,6-Br₂-C₆H₃-N(CH₂OCH₃)-NO₂ | 500 | 89 |
| (2,6-Cl₂-C₆H₃-N=N-O⁻)·(C₆H₅-N⁺H₂-C(CH₃)₃)(O) | 500 | 100 |
| 2,4-(NO₂)₂-3,5-(CH₃)₂-6-? -N(CH(CH₃)C₂H₅) | 500 | 89 |
| 2,6-Cl₂-C₆H₃-N(CH₃)-NO₂ | 500 | 100 |
| 2,3,5,6-Cl₄-C₆H-N(COCH₃)-NO₂ | 500<br>200<br>100<br>50 | 100 (Sl)<br>95<br>95<br>95 |
| 2,3,5,6-Cl₄-C₆H-N(CH₂-CO-OCH₃)-NO₂ · ½H₂O | 500 | 84 |
| (2,3,5,6-Cl₄-C₆H-N=N-O⁻)·N(CH₃)₄⁺ (O) | 200<br>100<br>50<br>25<br>12.5 | 98<br>96<br>87<br>71<br>71 |
| 2,3,5-Cl₃-C₆H₂-NH-NO₂ | 500 | 84 (Sl) |
| (2,3,5-Cl₃-C₆H₂-N=N-O⁻)·NH₄⁺ · 2H₂O (O) | 500 | 84 (Sl) |

Sl = Slight phytotoxicity
M = Moderate phytotoxicity
Sv = Severe phytotoxicity

EXAMPLE 11

Evaluation of the effectiveness of phenylnitramines in protectant control of leaf rust of wheat.

Individual pots of approximately 20 to 25 wheat (*Triticum vulgare*, cv. Cheyenne) plants each, grown under greenhouse conditions, approximately 7 to 8 days old and 10.2 to 12.7 cm. tall are used as test plants, a minimum of three such pots per unit of test.

The required amount of test compound is dissolved in 10 ml. of a stock solution consisting of 1995 ml. acetone, 4 ml. sorbitan trioleate and 1 ml. polyoxyethylene (20) sorbitan monooleate and diluted to a volume of 100 ml. by addition of 90 ml. deionized water.

Test plants, three pots per unit of test, are mounted on a compound turntable and sprayed to incipient run-off with the test solution applied at 2.81 kg/cm² pressure for 60 seconds using a solid conte T-Jet 8801E spray nozzle. By this spray procedure the delivery rate is equivalent to approximately 467.7 l/ha.

Treated plants are allowed to air dry for 5 to 6 hours and then inoculated by uniformly dusting with urediospores of leaf rust of wheat (*Puccinia recondita* var. *tritici*) at a rate of approximately $2 \times 10^5$ urediospores per replicate, using urediospores directly from diseased plants. Inoculated plants are immediately placed in an incubation chamber maintained at 21° C. and 95% + RH. After 24 hours plants are removed to the greenhouse and maintained under greenhouse conditions of 21° to 29.4° C. and 50 to 75% RH for 5 to 8 days until signs of orange pustules visible to the naked eye appear on the inoculated but otherwise untreated controls.

Effectiveness of the compound, as applied, is expressed as Percent Control calculated as:

$$\text{Percent Control} = 1.00 \frac{\text{Ave. No. of Pustules on all treated plants}}{\text{Ave. No. of Pustules on all untreated plants}} \times 100$$

Average number of pustules on plants of any given test unit is determined by randomly dividing all plants in each of the three replicates (one pot per replicate) into quadrants, counting the actual number of pustules on all plants within a quadrant in each of the three replicates, multiplying by four and averaging the total number of pustules thus obtained as the average number of pustules per replicate.

TABLE VII

Effectiveness of Phenylnitramines in Protectant Control of Leaf Rust of Wheat

| Compound | Rate of Application (ppm) | No. of Infection Loci/Replicate Rep. 1 | Rep. 2 | Rep. 3 | Percent Control: Plant Injury (Ave) |
|---|---|---|---|---|---|
| 2,3,5,6-Tetrachloro-N-nitroaniline | 200<br>100<br>50 | 81<br>124<br>186 | 96<br>119<br>173 | 86<br>116<br>199 | 69:0<br>58:0<br>35:0 |
| Infected, untreated controls | — | 251 | 290 | 316 | |

What is claimed:

1. A method for the control of fungi, comprising contacting said fungi with a fungicidally effective amount of a compound selected from formulae (I) and (III):

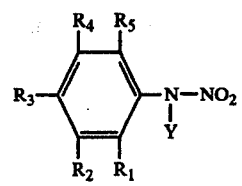

(I)

and 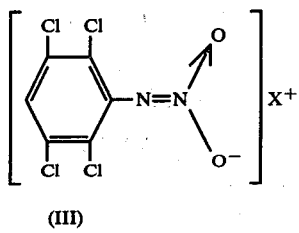

(III)

wherein the formula (I) R groups $R_1$ to $R_5$ each represent a member selected from the group consisting of hydrogen, halogen, $C_1$-$C_4$ alkyl, halo($C_1$-$C_4$) alkyl, $C_1$-$C_4$ alkylthio, $C_1$-$C_4$ alkylsulfonyl, $C_1$-$C_4$ alkanoylamino,

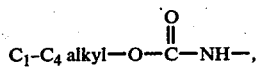

cyano and nitro; Y is a member selected from the group consisting of hydrogen, $C_1$-$C_8$ alkyl, $C_3$-$C_8$ alkenyl,

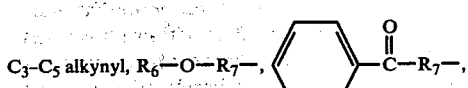

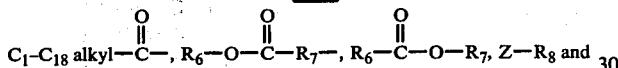

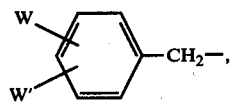

wherein
$R_6$ is $C_1$-$C_4$ alkyl, $C_3$-$C_5$ alkenyl or $C_3$-$C_5$ alkynyl; $R_7$ is $C_1$-$C_4$ alkylene; $R_8$ is $C_2$-$C_4$ alkylene; W and W' each are hydrogen or halogen; Z is hydroxy or halogen; with the provisos, that at least two of the R groups $R_1$ to $R_5$ are other than hydrogen; and that not more than two of the R groups $R_1$ to $R_5$ are $C_1$-$C_4$ alkylthio, $C_1$-$C_4$ alkylsulfonyl or nitro; and wherein the formula (III) cation X represents a member selected from the group $H_3NR'$, $H_2NR'R''$, $HNR'R''R'''$, and $NR'R''R'''R''''$. wherein the R groups R' to R'''' each represent a member selected from $C_1$-$C_{18}$ alkyl, aryl and benzyl, and where R' and R'' taken together with the nitrogen to which they are attached form a cyclic moiety selected from

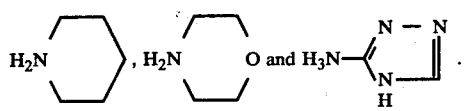

2. A method according to claim 1, wherein the formula (I) R groups $R_1$ to $R_5$ each are selected from hydrogen, $C_1$-$C_2$ alkyl, $C_2$-$C_3$ alkanoylamino,

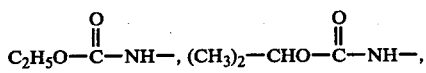

cyano, nitro, trifluoromethyl, methylthio and methylsulfonyl; Y is selected from $C_1$-$C_8$ alkyl, $C_1$-$C_{18}$ alkyl-

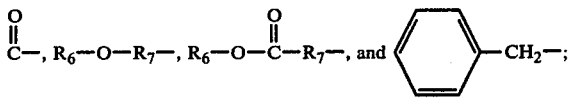

wherein $R_6$ is $C_1$-$C_4$ alkyl; $R_7$ is $C_1$-$C_4$ alkylene; and wherein the formula (III) cation X is selected from $(CH_3)_4N$, $(n$-$C_4H_9)_3NH$, $n$-$C_{12}H_{25}NH_3$, $C_{18}H_{35}NH(CH_3)_2$,

3. A method according to claim 1, wherein $R_1$ is selected from hydrogen, methyl, ethyl, bromine, chlorine, iodine, trifluoromethyl and nitro; $R_2$ is selected from hydrogen, methyl, bromine, chlorine, cyano and trifluoromethyl; $R_3$ is selected from hydrogen, methyl, bromine, chlorine, cyano, nitro, trifluoromethyl, $C_2$-$C_3$ alkanoylamino, methylthio, methylsulfonyl, ethylcarbamate and isopropylcarbamate; $R_4$ is selected from hydrogen, bromine, chlorine and trifluoromethyl; $R_5$ is selected from hydrogen, methyl, ethyl, bromine, chlorine and nitro; Y is selected from hydrogen, $CH_3$—, $C_2H_5$—, $(CH_3)_2CH$—,

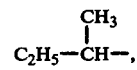

$n$-$C_8H_{17}$ $CH_2=CH-CH_2-$, $CH\equiv C-CH_2-$,

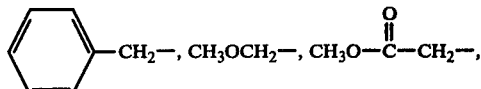

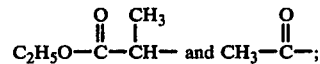

and wherein the formula (III) cation X is selected from the group consisting essentially of $(CH_3)_4N$, $(n$-$C_4H_9)_3NH$, $n$-$C_{12}H_{25}NH_3$, $C_{18}H_{35}NH(CH_3)_2$, $C_{18}H_{37}NH(CH_3)_2$,

4. A method according to claim 1, wherein $R_1$ is selected from hydrogen, bromine and chlorine; $R_2$ is selected from hydrogen and chlorine, $R_3$ is selected from hydrogen, methyl, bromine, chlorine, nitro, trifluoromethyl,

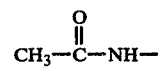

and methylsulfonyl; $R_4$ is selected from hydrogen and chlorine; $R_5$ is selected from hydrogen, bromine and chlorine; Y is selected from hydrogen, $(CH_3)_2CH$—,

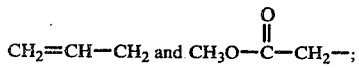

wherein the formula (III) cation X is selected from (n-C₄H₉)₃NH, n-C₁₂H₂₅NH₃, C₁₈H₃₅NH(CH₃)₂,

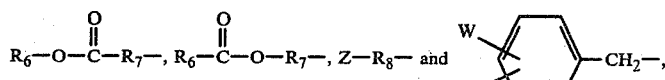

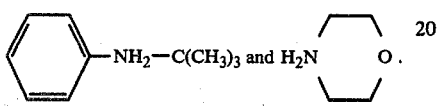

5. A method according to claim 1, wherein said compound is 2,3,5,6-tetrachlorophenylnitramine.

6. A method according to claim 1, wherein said compound is N-acetyl-2,3,5,6-tetrachlorophenylnitramine.

7. A method according to claim 1, wherein said compound is N-isopropyl-2,3,5,6-tetrachlorophenylnitramine.

8. A method according to claim 1, wherein said compound is N-propynyl-2,3,5,6-tetrachlorophenylnitramine.

9. A method according to claim 1, wherein said compound is the salt of 2,3,5,6-tetrachlorophenylnitramine where X is (CH₃)₄N.

10. A method according to claim 1, wherein said compound is 2,4,6-tribromophenylnitramine.

11. A method according to claim 1, wherein said compound is the salt of 2,3,5,6-tetrachlorophenylnitramine where X is (n-C₄H₉)₃NH.

12. A method according to claim 1, wherein said compound is the salt of 2,3,5,6-tetrachlorophenylnitramine where X is

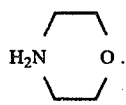

13. A method for protecting living plants from attack by fungi, comprising applying to the foliage of said plants a fungicidally effective amount of a compound selected from formulae (I) and (III):

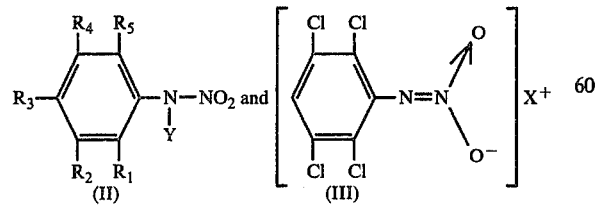

wherein the formula (I) R groups R₁ to R₅ each represent a member selected from the group consisting of hydrogen, halogen, C₁-C₄ alkyl, halo(C₁-C₄)alkyl, C₁-C₄ alkylthio, C₁-C₄ alkylsulfonyl, C₁-C₄ alkanoylamino, C₁-C₄ alkyl- C₁-C₄ alkyl-O-C(=O)-NH-, cyano and nitro; Y is a member selected from the group consisting of hydrogen, C₁-C₈ alkyl, C₃-C₅ alkenyl,

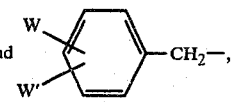

wherein R₆ is C₁-C₄ alkyl, C₃-C₅ alkenyl or C₃-C₅ alkynyl; R₇ is C₁-C₄ alkylene; R₈ is C₂-C₄ alkylene; W and W' each are hydrogen or halogen; Z is hydroxy or halogen; with the provisos, that at least two of the R groups R₁ to R₅ are other than hydrogen; and that not more than two of the R groups R₁ to R₅ can be C₁-C₄ alkylthio, C₁-C₄ alkylsulfonyl or nitro; and wherein the formula (III) cation represents a member selected from the group H₃NR', HNR'R''R''' and NR'R''R'''R'''', wherein the R groups R' to R'''' each represent a member selected from C₁-C₁₈ alkyl, aryl and benzyl, and where R' and R'' are taken together with the nitrogen they are attached to, they form a cyclic moiety selected from

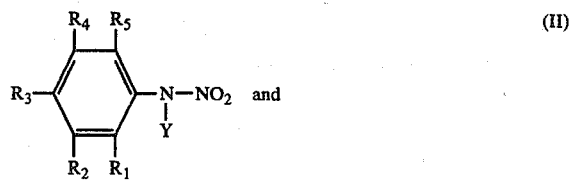

14. A method according to claim 13, wherein said compound is applied at a 10 ppm to 2000 ppm concentration as a liquid aqueous spray.

15. Compound of formulae (II) and (III):

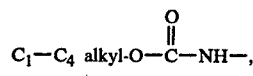

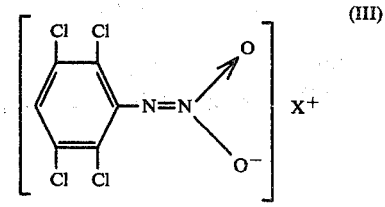

wherein the formula (II) R groups R₁, R₂, R₄ and R₅ each are selected from hydrogen, bromine and chlorine; R₃ is selected from hydrogen, $C_2$–$C_3$ alkanoylamino and $C_1$–$C_4$ alkyl-O–$\overset{\overset{O}{\|}}{C}$–NH–;

Y is selected from hydrogen, $C_3$–$C_5$ alkenyl, $C_3$–$C_5$ alkynyl, $C_1$–$C_{18}$ alkyl –$\overset{\overset{O}{\|}}{C}$–, $R_6$–O–$R_7$–, $C_1$–$C_4$ alkyl–O–$\overset{\overset{O}{\|}}{C}$–$R_7$–, Z—R—, wherein $R_6$ is $C_3$–$C_5$ alkenyl or $C_3$–$C_5$ alkynyl; $R_7$ is $C_1$–$C_4$ alkylene; $R_8$ is $C_2$–$C_4$ alkylene; Z is hydroxy or halogen; with the provisos, (1) that when Y is hydrogen, $R_3$ must be selected from $C_2$—$C_3$ alkanoylamino and $C_1$—$C_4$ alkyl –O–$\overset{\overset{O}{\|}}{C}$–NH–;

and (2) that at least two of the R groups $R_1$ to $R_5$ are other than hydrogen; and wherein the formula (III) cation X represents a member selected from the group $H_3NR'$, $H_2NR'R''$, $HNR'R''R'''$ and $NR'R''R'''R''''$, wherein the R groups R' to R'''' each represent a member selected from $C_1$–$C_{18}$ alkyl, aryl and benzyl, and when R' and R'' are taken together with the nitrogen they are attached to, they form a cyclic moiety selected from

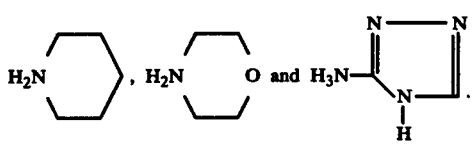

16. Compounds according to claim 15, wherein $R_1$ and $R_5$ are selected from bromine and chlorine; $R_2$ and $R_4$ are selected from hydrogen, bromine and chlorine; $R_3$ is selected from hydrogen, $C_2$–$C_3$ alkanoylamino, ethylcarbamate and isopropylcarbamate; Y is selected from hydrogen, $CH_3O$–$\overset{\overset{O}{\|}}{C}$–$CH_2$– and $CH_3$–$\overset{\overset{O}{\|}}{C}$–;

and wherein X is selected from $(CH_3)_4N$, $(n-C_4H_9)_3NH$, $n-C_{12}H_{25}NH_3$, $C_{18}H_{35}NH(CH_3)_2$, $CH_{18}H_{37}NH(CH_3)_2$,

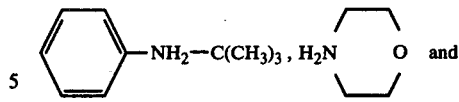

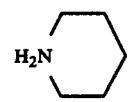

17. Compounds according to claim 15, wherein $R_1$ and $R_5$ each are chlorine, $R_2$, $R_4$ and Y are hydrogen; and $R_3$ is selected from acetamido, propionamido, ethylcarbamate and isopropylcarbamate.

18. Compounds according to claim 15, wherein $R_1$ and $R_5$ each are bromine; $R_2$, $R_3$ and $R_4$ each are hydrogen;

Y is selected from $CH_3O$–$\overset{\overset{O}{\|}}{C}$–$CH_2$– and $CH_3$–$\overset{\overset{O}{\|}}{C}$–.

19. Compounds according to claim 15, wherein $R_1$, $R_2$, $R_4$ and $R_5$ each are chlorine; $R_3$ is hydrogen; and Y is selected from $CH_2$=CH—$CH_2$—, CH≡C—$CH_2$—, $HOC_2H_4$—, Br—$C_2H_4$—, $CH_3O$–$\overset{\overset{O}{\|}}{C}$–$CH_2$–, $C_2H_5O$–$\overset{\overset{O}{\|}}{C}$–$\overset{\overset{CH_3}{|}}{CH}$– and $CH_3$–$\overset{\overset{O}{\|}}{C}$–.

20. Compounds according to claim 15, and represented by formula (III), wherein X is selected from $(CH_3)_4N$, $(n-C_4H_9)_3NH$, $n-C_{12}H_{25}NH_3$ and $C_{18}H_{35}NH(CH_3)_2$.

21. Compounds according to claim 15, and represented by formula (III), wherein X is selected from $C_{18}H_{37}(CH_3)_2$,

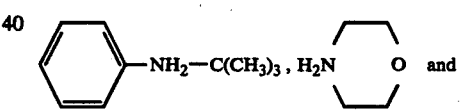

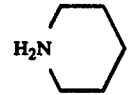

22. A compound according to claim 15, the salt of 2,3,5,6-tetrachlorophenylnitramine with $(CH_3)_4N$.

23. A compound according to claim 15, the salt of 2,3,5,6-tetrachlorophenylnitramine with $(n-C_4H_9)_3NH$.

24. A compound according to claim 15, the salt of 2,3,5,6-tetrachlorophenylnitramine with

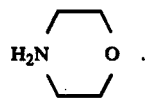

* * * * *